(12) United States Patent
Petoud et al.

(10) Patent No.: US 8,617,421 B2
(45) Date of Patent: Dec. 31, 2013

(54) LANTHANIDE METAL-ORGANIC FRAMEWORKS AND USES THEREOF

(75) Inventors: Stephane Petoud, Pittsburgh, PA (US);
Nathaniel L. Rosi, Pittsburgh, PA (US);
Kiley A. White, Pittsburgh, PA (US);
Demetra Anne Chengelis Czegan,
Greensburg, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 576 days.

(21) Appl. No.: 12/562,557

(22) Filed: Sep. 18, 2009

(65) Prior Publication Data

US 2010/0072424 A1    Mar. 25, 2010

Related U.S. Application Data

(60) Provisional application No. 61/136,607, filed on Sep. 18, 2008.

(51) Int. Cl.
*C09K 11/06* (2006.01)

(52) U.S. Cl.
USPC .................................................... 252/301.16

(58) Field of Classification Search
USPC ............. 252/301.16, 301.36; 534/15; 95/139;
424/9.36
See application file for complete search history.

(56) References Cited

U.S. PATENT DOCUMENTS

| 2005/0058604 A1* | 3/2005 | Raymond et al. | ............ | 424/9.36 |
| 2008/0121105 A1* | 5/2008 | Schubert et al. | ................ | 95/139 |

OTHER PUBLICATIONS

Mahata et al., 'A New Series of Three-Dimensional Metal-Organic Framework, [M2(H2O)][C5N1H3(COO)2]3-2H2O, M=La, Pr, and Nd: Synthesis, Structure, and Properties', Jan. 13, 2007, Inorganic Chemistry, 2007, vol. 46, pp. 1250-1258.*

Shi et al., 'Synthesis and crystal structrure of metal-organic frameworks [Ln2(pydc-3,5)3(H2O)9]n3NH2O (Ln=Sm, Eu, Gd, Dy' pydc-3,5=pyridine=3,5-dicarboxylate) along with the photoluminescent property of its europium one', Dec. 1, 2006, Journal of Molecular Structure, 837 (2007), pp. 185-189.*

Jian Zhang et al., "Sensitization of Near-Infrared-Emitting Lanthamide Cations in Solution by Tropolonate Ligands", Angew. Chem. 2005, 117, pp. 2564-2568.

Jian Zhang et al., "Sensitization of Near-Infrared-Emitting Lanthanide Cations in Solution by Tropolonate Ligands", Angew. Chem. Int. Ed., 2005, 44, pp. 2508-2512.

Christina Stammal et al., "Synthesis and X-ray Analysis of New [5]Helicenes—HMO Calculations on the Photocyclization of the Stilbene Precursors", Eur. J. Org. Chem. 1999, pp. 1709-1718.

* cited by examiner

*Primary Examiner* — Emily Le
*Assistant Examiner* — Lynne Edmondson
(74) *Attorney, Agent, or Firm* — Foley & Lardner LLP

(57) ABSTRACT

Metal-organic frameworks (MOFs) are crystalline porous materials that include metal ions linked together into periodic structures via organic ligands. MOFs that contain lanthanide ions are a new class of visible and near-IR luminescent materials, suitable for a broad range of applications. For example, the MOF framework afforded by 2,5-dimethoxy-1,4-phenylene)di-2,1-ethenediyl]bis-carboxylate is associated with unusually long luminescence lifetimes. Thus, a complex of this ligand with a lanthanide provides a sharp emission profile, coupled with a comparatively long signal lifetime, for an unusually high luminescence. More generally, lanthanide-MOF systems exhibit several advantages that are ideal for barcoded materials, due to the photophysical attributes of lanthanide cations and the well-defined organization of the MOF structure.

19 Claims, 2 Drawing Sheets
(2 of 2 Drawing Sheet(s) Filed in Color)

LANTHANIDE METAL-ORGANIC FRAMEWORKS AND USES THEREOF

This application claims priority from U.S. Provisional Application No. 61/136,607, filed Sep. 18, 2008, incorporated herein by reference in its entirety.

BACKGROUND OF THE INVENTION

New methods for lanthanide sensitization are of great interest due to the incorporation of lanthanide luminescence in a portfolio of applications, including photonic materials, liquid lasers, and telecommunication devices. Near-IR (NIR)-emitting lanthanides are of particular interest for biological imaging because of their advantageous electronic properties compared to that of common organic fluorophores.

Lanthanide emission bands are sharp, occur at fixed wavelengths, and are not affected by environmental factors such as pH or temperature. Accordingly, they are easily detected and discriminated from background signals. Lanthanide cations also have long luminescence lifetimes and are highly resistant to photobleaching, allowing for extended storage time and repeated exposure to excitation sources.

Since f-f transitions are Laporte-forbidden, however, free lanthanide cations have extremely low absorptivity, which limits their luminescence intensity. To overcome this limitation, an "antenna effect" has been exploited to improve the efficiency of lanthanide luminescence. By this approach, lanthanide cations are complexed with "antennae," i.e., molecules with high absorptivity that can transfer their absorbed energy to sensitize the lanthanide cations.

Different strategies have been applied to sensitize NIR-emitting Ln, including use of dendrimer and nanocrystalline forms. The organization of the antennae about the lanthanide cation significantly impacts the luminescent properties of the complex. Ideally, lanthanides should be effectively shielded from water (O—H) vibrations for sufficient luminescence lifetimes and for discrimination from background signals.

These challenges are hard to overcome because lanthanide cations generally exhibit low stereochemical requirements. Accordingly, it has proven difficult to control the organization of the ligands in a prescribed manner.

SUMMARY OF THE INVENTION

The inventors have addressed this problem through a supramolecular approach, in which the ligand is purposefully designed to have a coordination environment that meets the requirements for lanthanide cations. By this approach, metal-organic framework (MOF) materials are a means not only to sensitize lanthanides but also to optimize their excitation and emissive properties.

MOFs are a relatively new class of porous materials that are made up of metal ions or clusters, which are linked together into periodic two or three dimensional lattices via multitopic organic ligands. The metals and ligands can be chosen to impart specific function to the MOF.

Numerous lanthanide-containing MOFs have been synthesized, and sensing applications based on their visible emission properties have been exploited. On the other hand, MOFs have not been designed heretofore to sensitize and optimize the photophysical properties NIR-emitting lanthanides specifically.

The present invention exploits certain features of MOFs in order to improve lanthanide sensitization in the NIR. First, MOFs can have rigid architectures in which the metals and ligands are well-organized and constrained in space. Second, MOFs can adopt a variety of topologies, and in some cases the topological features of a MOF can be designed in an a priori fashion.

To date MOFs have been designed for gas storage and sequestration, catalysis, and separations, among other applications. The present inventors report a new approach for generating "barcoded" systems that utilize MOFs, containing multiple near-infrared (NIR) emitting lanthanides, that are characterized by well-controlled composition and photophysical properties. Furthermore, MOFs have well-defined crystalline structures, which accommodate incorporation of multiple different cations and organic sensitizers with a high degree of spatial organization. The crystalline nature of these materials allows for unambiguous rationalization of the luminescence properties, based on the specialized structures described here.

A preferred MOF framework is afforded by 2,5-dimethoxy-1,4-phenylene)di-2,1-ethenediyl]bis-carboxylate, a ligand associated with unusually long luminescence lifetimes in the NIR range. Thus, a complex of this ligand with a lanthanide provides a sharp emission profile in the NIR, coupled with a comparatively long signal lifetime, for an unusually high luminescence.

More generally, the inventors have discovered that lanthanide-MOF systems exhibit several advantages making them ideal as barcoded materials, due to the photophysical attributes of lanthanide cations and the well-defined organization of the MOF structure. Such systems provide an conclusive way to recognize the identity of an object or a biological entity. To this end, highly reproducible, barcoded MOF materials are provided that, in accordance with the invention, display NIR emissions based on ratiometric control of lanthanide composition within the MOFs.

Furthermore, multiple different lanthanide cations can be incorporated yielding highly reproducible barcoded MOF materials with NIR emissions based on control of the relative lanthanide ratios within the MOFs.

For practical applications, barcoded materials must be incorporated into objects, e.g. money or an article of clothing, in ways that do not detrimentally affect their signal. The inventors have demonstrated barcoded MOF materials, pursuant to the invention, are characterized by such robustness in marking usage.

The inventors also have validated a MOF approach for generating barcoded materials that is based on the sharp emission of lanthanide cations. That is, they devised a new system that is useful for preparing polymetallic lanthanide compounds that simultaneously emit several independent luminescence signals. Pursuant to the invention, one can predict and control the lanthanide composition of the material and, hence, the resulting emission intensities, by varying the synthetic conditions. For instance, it is shown that excitation at a single wavelength produces concurrent ytterbium and erbium emission bands that are linearly correlated to the lanthanide ratio. In this regard, $Er_xYb_{1-x}$-PVDC-1 MOFs illustrate the properties that typify barcoded luminescent materials of the invention, which have a myriad of marking uses for practical application.

In accordance with one aspect of the invention, therefore, a composition is provided that comprises a lanthanide and an organic ligand that is complexed to the lanthanide, where the ligand has multiple metal-binding sites and an electronic structure that accommodates transfer of energy to the lanthanide. In a composition of the invention, the ligand can be complexed to at least two, three or more different lanthanides, such as erbium, ytterbium, and neodymium. Exemplary of other, suitable lanthanides are samarium, holmium, thulium, praseodymium and dysprosium, which also are NIR-emitting cations, as well as europium, terbium, and gadolinium.

In a preferred embodiment, the ligand is (4,4'-[(2,5-dimethoxy-1,4-phenylene)di-2,1-ethenediyl]bis-carboxylate). Thus, a composition of the invention can have the formula:

$(Er_xYb_y)_2(4,4'$-[(2,5-dimethoxy-1,4-phenylene)di-2,1-ethenediyl]bis-carboxylate$)_3$, where x is a number between 0 and 1 and y is a number having a value equal to (1−x). In such a composition, therefore, x could be 0.81, 0.7, 0.58, or 0.32 and y could be 0.19, 0.3, 0.42, or 0.68, inter alia.

According to another aspect, the invention provides a method for marking an object with a metal-organic complex. The inventive methodology comprises:

(a) providing a composition comprised of at least one metal-organic complex that comprises an organic ligand and at least two different lanthanides, wherein said lanthanides are present in a predetermined ratio and wherein said ligand has multiple metal-binding sites and an electronic structure that accommodates transfer of energy to said lanthanides; and then (b) applying said composition to said object. In such a method, pursuant to the invention, the applying can comprise loading a device with said composition and then using said device to mark said object with said composition.

In accordance with yet another aspect, a method is provided for preparing a metal-organic complex. The method comprises: (a) providing an organic ligand that binds to a lanthanide, wherein said ligand has multiple metal-binding sites and an electronic structure that accommodates transfer of energy to said lanthanide; (b) reacting said ligand and at least one lanthanide in a reaction mixture to form a metal-organic complex, such that the distance between said ligand and said lanthanide in said complex is controlled; and then (c) crystallizing said complex from said reaction mixture, forming crystals of said complex. In a further step, the crystals thus formed may be isolated from the reaction mixture.

BRIEF DESCRIPTION OF THE DRAWINGS

The application contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Typically, lanthanides are sensitized by means of small molecules. In contrast, the present invention sensitizes lanthanides through the use of MOFs, which characteristically are porous, crystalline solid-state materials. In accordance with the invention, MOFs allow the formation of luminescent compounds that contain a large number of lanthanide cations per unit of volume, resulting in increased luminescence signal. Thus, MOFs provide a unique means for effecting better control of ligand (sensitizer) geometry around the lanthanide metal. Moreover, MOFs provide for effectively shielding the lanthanide ions from certain solvents that may quench the luminescence. Lanthanide cations need to be sensitized by an appropriate antenna, in order to emit an appropriate signal. Pursuant to the invention, MOFs allow an improved control of such sensitization through modification of the excitation wavelength; this, due to the rigidity of the structures and preorganization of intermolecular interactions to lower the excitation energy.

The inventors initially identified a ligand that could both effectively sensitize the NIR emission of $Yb^{3+}$ and promote its assembly into an extended porous network. 4,4'-[(2,5-dimethoxy-1,4-phenylene)di-2,1-ethenediyl]bis[benzoic acid] ($H_2$-PVDC) was selected because of its strong absorptivity in the visible, its length, which could promote the formation of large, accessible pores, and the fact that it was capable of sensitizing the NIR emission of $Yb^{3+}$ (see below). The inventors chose to target MOFs with infinite Yb-carboxylate chains or infinite secondary building units (SBUs). Infinite SBUs force the ligands into parallel packing arrangements and they are known to promote the formation of non-interpenetrated structures, regardless of the length of the linker. Several lanthanide-based MOFs exhibiting infinite SBUs have been constructed previously.

Figure 1:
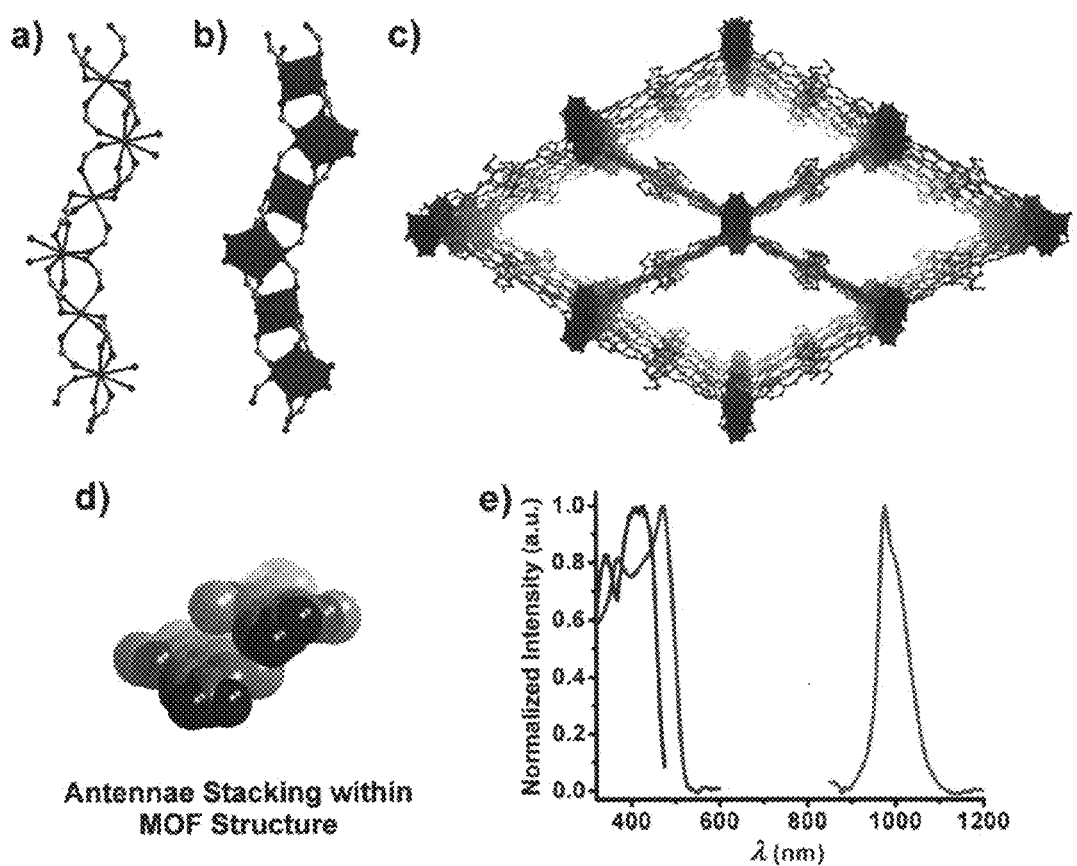
FIG. 1 presents structural and spectral data for Yb-PVDC-1. There are a ball-and-stick depiction of infinite SBU (a) and SBU with $Yb^{3+}$ represented as polyhedra (b) (C, grey; O, red; $Yb^{3+}$, dark green); a projection view of the framework, seen along the a crystallographic direction (c); a ligand stacking motif along [110] (d); and luminescent data comparing the excitation profiles of the Yb-PVDC molecular complex (red; $\lambda_{em}$=980 nm) to Yb-PVDC-1 (blue; $\lambda_{em}$=980 nm) and displaying the $Yb^{3+}$ emission (green; $\lambda_{em}$=470 nm), collected upon excitation of Yb-PVDC-1 (e).

As described in greater detail below, reacting Yb$(NO_3)_3 \cdot 5H_2O$ with $H_2$-PVDC yielded Yb-PVDC-2, formulated as $Yb_2(C_{26}H_{20}O_6)_3 \cdot (DMF)_{12}(H_2O)_{10}$. Yb-PVDC-2 crystallizes in the orthorhombic Pnna spacegroup, and it also exhibits infinite Yb-carboxylate SBUs. The SBU is composed of alternating octa- and hexa-coordinated $Yb^{3+}$. The $Yb^{3+}$ are bridged by two carboxylates, in a di-mondodentate fashion, and a third carboxylate, which chelates the octa-coordinate $Yb^{3+}$ and coordinates in a monodentate fashion to the hexa-coordinate $Yb^{3+}$ (FIGS. 1a,b).

These coordination modes result in a chain of corner-sharing polyhedral $Yb^{3+}$. Each chain is linked to a total of six other chains via the phenylenevinylene portion of the PVDC linkers. The ligands that connect the chains along the [001] stack in parallel with one another, while the ligands that connect the chains in the [011] form pairs that criss-cross with one another, resulting in close π-π interactions between the central phenyl rings of the PVDC linkers (FIG. 1c). Each infinite SBU is connected to six other SBUs, resulting triangular channels that measure approximately 13-14 Å from corner to edge.

In order to determine how the MOF structure affects the luminescent properties of the Yb-PVDC system, the absorbance, emission, and excitation of PVDC and the Yb-PDC complex were measured. (See example below for details on the preparation of Yb-PVDC.) Due to solubility constraints, it was necessary to use DMSO as the solvent for these experiments.

Figure 2:
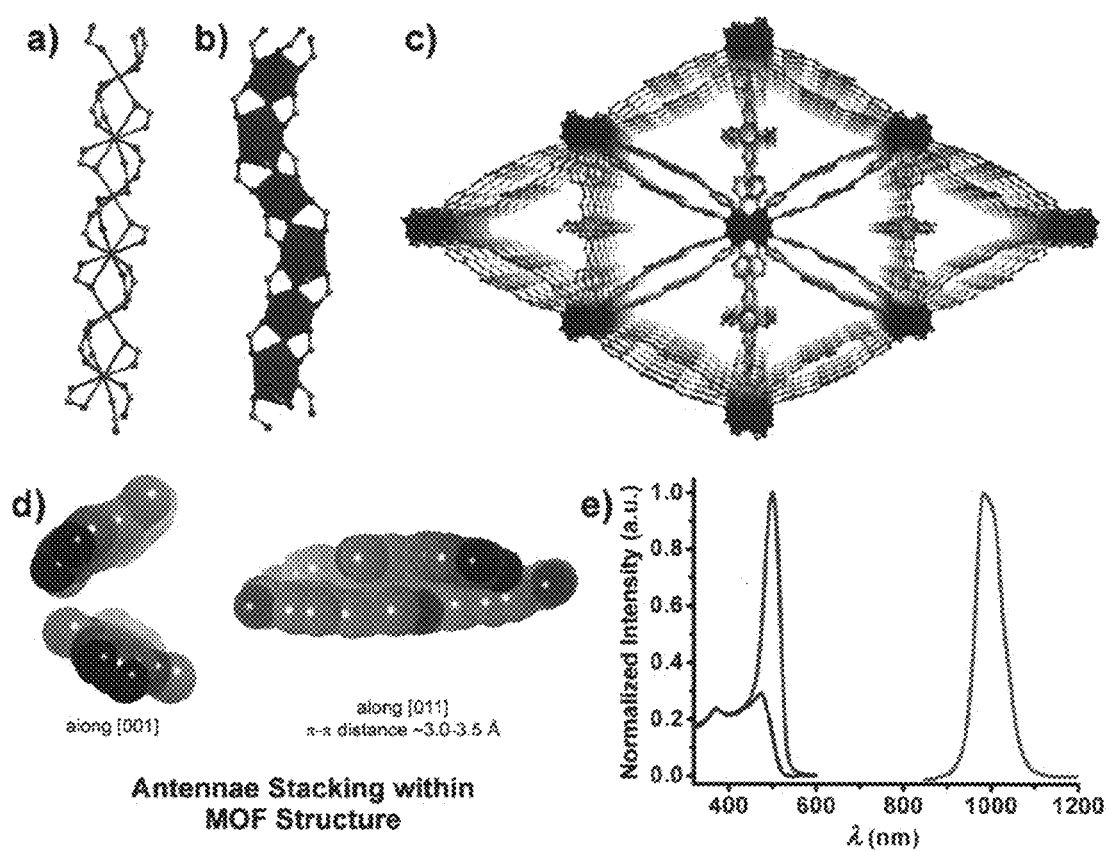
FIG. 2 presents structural and spectral data for Yb-PVDC-2. There are a ball-and-stick depiction of infinite SBU (a) and SBU with $Yb^{3+}$ represented as polyhedra (b); a projection view of the framework, seen along the a crystallographic direction (c); ligand stacking motifs (d) (C, grey; O, red; Yb3+, dark green); and luminescent data comparing the excitation profiles of Yb-PVDC-1 (red; $\lambda_{em}$=980 nm) to Yb-PVDC-2 (blue; $\lambda_{em}$=980 nm) and displaying the $Yb^{3+}$ emission (green; $\lambda_{ex}$=500 nm), collected upon excitation of Yb-PVDC-2 (e).

As shown in FIG. 2, the absorbance spectrum of PVDC displays two bands centered at 340 and 415 nm. Excitation through either of these bands produces a fluorescence band centered at 485 nm and the excitation spectrum on this fluorescence band shows a profile similar to the absorbance spectrum. As illustrated in FIG. 2, the Yb-PVDC complex displays $Yb^{3+}$ emission in the NIR range, with the typical band maxima of 980 nm. The excitation spectrum of $Yb^{3+}$ emission (FIG. 2) displays two bands, centered at 340 and 415 nm, the same profile as the absorbance of PVDC, indicating that $Yb^{3+}$ is sensitized effectively by PVDC via the antennae effect.

Luminescence analysis of MOF Yb-PVDC-1 was performed with a crystalline MOF sample kept under chloroform. The MOF Yb-PVDC-2 also displayed $Yb^{3+}$ luminescence (FIG. 2). In contrast to $Yb^{3+}$ excitation in complex with PVDC in solution, however the MOF excitation was notably red-shifted, displaying three bands with maxima at 280, 370, and 510 nm, illustrated in FIG. 2.

The close π-π interactions between the PVDC in Yb-PVDC-2 results, it is believed, in a decrease in the π→α-□ transition of the ligand, thus causing a decrease in the excitation energy. In accordance with the invention, therefore, imparting specific ligand-ligand interactions in the context of a MOF can produce low energy excitation pathways for NIR antennae.

The structure of the MOF induces the lowering of the excitation wavelength, which allows for more sensitive detection in biological media by decreasing biological fluorescence background. This is so because naturally occurring molecules tend to have an excitation wavelength, located higher in energy.

One application for these NIR-emitting MOFs is as bio-imaging reagents. The size of the MOF could be controlled via the addition of surfactant during synthesis, thus creating nano-scale MOFs. The nano-scale MOFs could be coated into a silica bead, which then could be functionalized to impart biocompatibility and recognition abilities.

For Yb-PVDC-1, it was possible to excite ytterbium emission at wavelengths up to ~510 nm; and for Yb-PVDC-2, wavelengths of up to ~540 nm were achieved. These are much lower in energy than the wavelengths possible for the complexes formed with $Yb^{3+}$ and $H_2$-PVDC, which gives the MOFs a major advantage that is impossible to be obtained with organic fluorophores or with semiconductor nanocrystals (quantum dots). It is likely the MOF structure improves the rigidity of the aromatic chromophoric groups, thus lowering the electronic energy states of the chromophoric groups. It also is feasible, as demonstrated through Yb-PVDC-2, to achieve structural arrangements with close π-π interactions, further lowering the energy necessary for sensitization while at the same time improving the efficiency.

Lower excitation energy has two main benefits for a bio-imaging application. First, there are many naturally occurring luminescent species in biological media, most of which are excited in the ultra-violet to blue range [200-375 nm]. The native fluorescence background often is referred to as "autofluorescence." Most conventional bio-imaging reagents also are excited in this range, and their fluorescence is difficult to distinguish from the autofluorescence, thus reducing sensitivity. Furthermore, since much of the incident excitation light is absorbed by the biological media in addition to the imaging reagent, more intense excitation source is necessary to achieve sufficient absorption for detectable fluorescence. Shifting excitation wavelengths to 500 nm significantly reduces the amount of autofluorescence generated by biological media, thus the luminescence of the MOFs could be detected with improved sensitivity using a less intense excitation source.

Secondly, it would be ideal to achieve excitation at wavelengths in the NIR window, >640 nm. In this range, light can deeply penetrate through biological tissue such as skin and blood, allowing for in vivo applications. With the invention, it is demonstrated that the excitation wavelengths can be red-shifted through appropriately designed MOFs. By choosing a different chromophoric group with lower energy absorption than $H_2$PVDC, it should be possible to use the MOF strategy to achieve excitation at the desired 640 nm or higher wavelength.

In this description, the term "object" denotes an article of manufacture including but not limited to parcels, mechanical parts, biological samples, electronic chip cards, check cards, credit cards, identity cards, bank notes, certificates, documents and the like.

The term "composition" denotes one or more lanthanides bound or coordinated to an organic compound capable of binding to a lanthanide, and additionally including water and/or organic solvent.

The term "device" here refers to a printing system, stamp, rollerball pen, fountain pen, felt-tip pen, dip pen, paint brush, ink jet printer, spinneret, clear tube or similar small clear container and the like.

In the present context, the term "ligand" denotes any organic compound that: (A) binds to a lanthanide; (B) has multiple metal-binding sites and, hence, is capable of binding more than one type of lanthanide, if desired; and (C) an electronic structure that accommodates transfer of energy from the ligand to a complexed lanthanide, sensitizing the latter, e.g., via electron transfer, a Dexter Mechanism, or a dipole-dipole interaction. Illustrative of this category are ligands that are substituted triphenylene compounds, substituted pyrenes, fluorescein anions, eosin anions, erythrosine anions, fluorexon anions, substituted poly(pyrazole) borates, substituted podate anions, Lehn cryptands, porphyrins, 1,3-diketonates, pyridines, polypyridines and related derivatives, dipicolinates and related derivatives, hydroxyquinolines and related derivatives, and (4,4'-[(2,5-dimethoxy-1,4-phenylene)di-2,1-ethenediyl]bis-carboxylate).

The phrase "predetermined ratio" denotes the relative ratios of multiple near-infrared (NIR) emitting lanthanides, that are characterized by well-controlled composition and photophysical properties. Specifically, the ratio of different lanthanides control the characterization of the photophysical properties as to afford a signal that is employed to distinguish one marked object from each other. Objects marked with multiple different, NIR-emitting lanthanide compositions containing different ratios of different lanthanides can be distinguished spectroscopically.

The terms "mark" and "marked" denote the result of applying a composition of the invention to an object.

In this regard, "crystallizing" refers to a process or separation technique in which solute from the liquid solution is precipitated in a crystalline phase.

The term "isolating" here means that when isolated (e.g., from other components of a synthetic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of an Lanthanide Compound by weight of the isolate. In one embodiment, the isolate contains at least 95% of an Lanthanide Compound by weight of the isolate.

The invention is described further below, by reference to the following examples, which are illustrative only.

EXAMPLE I

Phenylene Derivative Barcoded Metal Organic Frameworks Containing Varied $Yb^{3+}$ and $Er^{3+}$ Stoichiometries Two illustrative, $Yb^{3+}$-based MOFs, Yb-PVDC-1 and Yb-PVDC-2, can be tuned and optimized in relation to the photophysical properties of $Yb^{3+}$ by tailoring MOF architecture. In addition, these materials have long luminescence lifetimes and high quantum yields compared to other $Yb^{3+}$-based systems under solvent.

The synthesis of Yb-PVDC-1 can be modified in accordance with the invention to yield barcoded frameworks containing both ytterbium and erbium. $Yb^{3+}$ and $Er^{3+}$ were chosen because they have very distinct emission profiles in the NIR. Specifically, we reacted $H_2$-PVDC (4,4'-[(2,5-dimethoxy-1,4-phenylene)di-2,1-ethenediyl]bis-benzoic acid), our chosen antenna, with $Er(NO_3)_3 \cdot 5H_2O$ and $Yb(NO_3)_3 \cdot 5H_2O$ to produce yellow needles of four luminescent frameworks with varying lanthanide metal stoichiometries: (1) $Er_{0.32}Yb_{0.68}$-PVDC-1; (2) $Er_{0.58}Yb_{0.42}$-PVDC-1; (3) $Er_{0.70}Yb_{0.30}$-PVDC-1; and (4) $Er_{0.81}Yb_{0.19}$-PVDC-1.

EXAMPLE II

Phenylene Derivative Metal Organic Framework as Scaffold Antenna for $Yb^{3+}$

Two MOF structures are presented, both using $Yb^{3+}$ and a phenylene derivative organic chromophoric group. This ligand has not been used previously for the synthesis of MOFs, and its structure, as well as the structure of the resulting MOF complex, has not been described heretofore.

These two MOFs, Yb-PVDC-1 and Yb-PVDC-2, demonstrate that utilizing the MOF structural backbone in combination with NIR-emitting lanthanide cations, in accordance with the invention, results in a novel type of NIR-emitting material with superior luminescence properties: quantum yields values among the highest reported in the literature and these MOFs have longer luminescence lifetimes, i.e., more than twice the value observed for comparable NIR-emitting lanthanide complexes. These superiorities in luminescence quantum yields, and lifetimes will result in a significant increase in detection sensitivity. Such advantage cannot be obtained with organic fluorophores, semiconductor nanocrystals, or "non-MOFS" lanthanide complexes.

I. Synthesis and Characterization

Initially, the inventors identified a ligand that could both sensitize NIR-emitting $Yb^{3+}$ and direct its assembly into an extended porous network. 4,4'-[(2,5-dimethoxy-1,4-phenylene)di-2,1-ethenediyl]bis-benzoic acid ($H_2$-PVDC) was chosen because it has strong absorptivity in the visible range because it could promote the formation extended MOF structures, and because preliminary studies indicated that it was capable of sensitizing NIR-emitting $Yb^{3+}$ (see below).

A. Synthesis of $H_2$-PVDC 1,4-Bis(bromomethyl)-2,5-dimethoxybenzene (1)

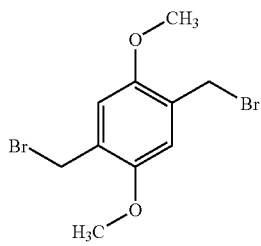

This intermediate was prepared following Zhang et al., *Angew. Chem.*, 117: 2564 (2005); *Angew Chem. Int'l Ed.* 44: 2508 (2005), as detailed here. To a stirred solution of 1,4-dimethoxybenzene (Aldrich, 10.00 g, 72.37 mmol) in glacial acetic acid (Fisher, 50 mL), paraformaldehyde (Aldrich, 4.27 g, 144.75 mmol) and HBr/AcOH (Fluka, 33%, 30 mL) were added slowly. The mixture was stirred at 50° C. for one hour and hydrolyzed in water (200 mL) after cooling to room temperature. The white solid was collected by filtration, suspended in $CHCl_3$ (50 mL), and refluxed for 10 min. After cooling to room temperature, the white solid was again collected by filtration and washed with water (15.75 g, 67%).

$^1$H NMR (300 MHz, $CDCl_3$) δ 6.88 (s, 2H), 4.54 (s, 4H), 3.87 (s, 6H) ppm; $^{13}$C NMR (75 MHz, $CDCl_3$) δ 151.9, 128.0, 114.5, 56.9, 29.1 ppm; FTIR (KBr pellet): 2962 (w), 2934 (w), 2834 (w), 1509 (vs), 1461 (s), 1428 (s), 1404 (vs), 1319 (m), 1228 (vs), 1205 (s), 1179 (w), 1103 (w), 890 (w), 874 (w), 718 (w) $cm^{-1}$. HRMS (EI+) Calcd for $C_{10}H_{12}O_2Br_2$ $[M]^+$ 321.9204, found 321.9209.

2,5-Dimethoxy-1,4-phenylene)bis(methylene)bis (triphenylphosphonium bromide (2)

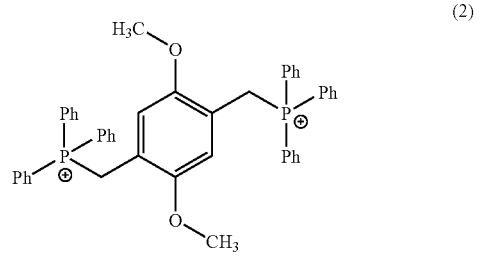 [SMILES: COc1cc(C[P+](c2ccccc2)(c2ccccc2)c2ccccc2)c(OC)cc1C[P+](c1ccccc1)(c1ccccc1)c1ccccc1]

A mixture of 1,4-bis(bromomethyl)-2,5-dimethoxybenzene 1 (9.59 g, 29.60 mmol) and triphenylphosphine (Aldrich, 18.63 g, 71.04 mmol) was refluxed in dry toluene (Acros, 99.8%, 80 mL) under argon for 6 hours. The crude white powder was obtained by filtration and used for subsequent reaction without further purification.

Dimethyl 4,4'-(1E,1'E)-2,2'-(2,5-dimethoxy-1,4-phenylene)bis(ethane-2,1-diyl)dibenzoate (3)

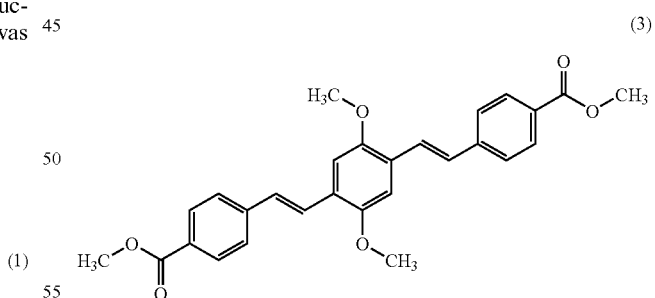

The following procedure was adapted from Stammel et al., *Eur. J. Org. Chem.* (1999), 1709. A mixture of (2,5-dimethoxy-1,4-phenylene)bis(methylene)bis (triphenylphosphonium bromide) 2 (25.68 g, 30.26 mmol) and methyl 4-formylbenzoate (TCI, 12.42 g, 75.66 mmol) was dissolved in dry methanol (Aldrich, 99.8%, 120 mL) under argon. NaOMe (Aldrich, 0.5 M in methanol, 160 mL) was added via cannula. A yellow precipitate formed immediately. The reaction was stirred under argon for 4 hours. After addition of water (140 mL), the yellow powder was filtered and washed with aqueous ethanol (60%,3×75 mL). Pure trans product was isolated via crystallization from toluene in the presence of few crystals of iodine (11.95 g, 86%) $^1$H NMR (300 MHz, CHCl$_3$) δ 8.02 (d, J=8.7, 4H), 7.59 (m, 6H), 7.16 (m, 4H), 3.95 (s, 6H), 3.93 ppm (s, 6H); $^{13}$C NMR (75 MHz, CHCl$_3$) δ 167.5, 152.4, 142.9, 130.6, 129.4, 128.8, 127.2, 127.0, 126.3, 109.9, 56.9, 52.66 ppm; FTIR (KBr pellet): 3007 (w), 2943 (w), 2835 (w), 1714 (vs), 1604 (m), 1493 (w), 1464 (w), 1437 (sh), 1410 (m), 1277 (vs), 1209 (s), 1183 (m), 1111 (s), 1041 (m), 1014 (w), 971 (trans =C—H, w), 875 (sh), 849 (w), 766 (m), 702 cm$^{-1}$ (w). HRMS (EI+) Calcd for C$_{28}$H$_{26}$O$_6$ [M]$^+$ 458.1729, found 458.1727

4,4'-(1E,1'E)-2,2'-(2,5-dimethoxy-1,4-phenylene)bis(ethene-2,1-diyl)dibenzoic acid (4)

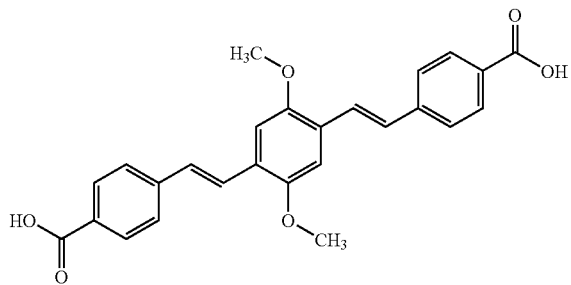

(4)

To dimethyl 4,4'-(1E,1'E)-2,2'-(2,5-dimethoxy-1,4-phenylene)bis(ethane-2,1-diyl)dibenzoate (5.46 g, 11.9 mmol) was added KOH (Alfa Aesar, 6.2 g, 121 mmol), methanol (60 mL), THF (60 mL), and H$_2$O (30 mL). The mixture was refluxed overnight, cooled, and H$_2$O (60 mL) was added, resulting in a clear yellow solution. The solution was acidified with 2N HCl and the resulting yellow solid was collected by filtration and was then recrystallized from DMF to yield a bright yellow powder (4.24 g, 83%). $^1$H NMR (300 MHz, DMSO) δ 12.87 (s, 2H), 7.95 (d, J=7.5, 4H), 7.70 (d, J=8.4, 4H), 7.51 (d, J=21.9, 2H), 7.45 (d, J=15.9, 2H), 7.39 (s, 2H), 3.93 ppm (s, 6H); $^{13}$C NMR (75 MHz, DMSO) δ 168.14, 152.30, 142.64, 130.94, 130.43, 129.33, 127.45, 126.94, 126.01, 110.59, 57.27 ppm; FTIR (KBr pellet): 2938 (b), 2831 (b), 2543 (m), 2361 (w), 1680 (C=O, s), 1600 (s), 1536 (w), 1491 (w), 1462 (m), 1315 (m), 1290 (s), 1209 (m), 1045 (m), 959 (trans =C—H, w), 859 (w), 771 cm$^{-1}$ (w). HRMS (EI+) Calcd for C$_{26}$H$_{22}$O$_6$ [M]$^+$ 430.1416, found 430.1401

B. Synthesis of Yb-PVDC-1 and Yb-PVDC-2

(i) Synthesis of Yb-PVDC-1: Yb$_2$(C$_{26}$H$_{20}$O$_4$)$_3$(H$_2$O)$_2$.(DMF)$_6$(H$_2$O)$_{8.5}$ In a glass vial (4 mL), a solution of 4,4'-(1EXE)-2,2'-(2,5-dimethoxy-1,4-phenylene)bis(ethene-2,1-diyl)dibenzoic acid (H$_2$-PVDC) (8.60 mg, 0.020 mmol) in DMF (0.4 mL) was added to a solution of Yb(NO$_3$)$_3$.5H$_2$O (6.75 mg, 0.015 mmol) and 1M HNO$_{3(aq)}$ (20.0 ☒ mL) in DMF (0.3 mL) to produce a neon green solution. The vial was capped and placed in an 85° C. isotemp oven for 48 hours to produce yellow crystalline needles of the product. The crystals were collected, washed with DMF (4×3 mL), and air dried (8.6 mg, 42.4%).

EA Calcd. (%) for Yb$_2$(C$_{26}$H$_{20}$O$_6$)$_3$(H$_2$O)$_2$.(DMF)$_6$(H$_2$O)$_{8.5}$: C, 51.04; H, 5.49; N, 3.72. Found: C, 50.97; H, 4.57; N, 3.91. EA. Calcd. (%) for the chloroform exchange product, Yb$_2$(C$_{26}$H$_{20}$O$_6$)$_3$(H$_2$O)$_2$.(CHCl$_3$)$_{2.75}$(DMF)$_{0.3}$: C, 48.61; H, 3.44; N, 0.21. Found: C, 48.79; H, 3.10; N, 0.21.

FT-IR (KBr 4000-700 cm$^{-1}$): 3432 (br), 2933 (w), 1665 (DMF C=O, m), 1600 (m), 1538 (s), 1414 (COO$^-$, vs), 1256 (w), 1209 (s), 1180 (w), 1106 (w), 1042 (s), 962 (m), 861 (w), 780 (trans C=C—H, s), 709 cm$^{-1}$(w).

(ii) Synthesis of Yb-PVDC-2: Yb2(C26H20O$_6$)3.(DMF)12(H2O)10

In a glass vial (20 mL), a solution of 4,4'-(1E,1'E)-2,2'-(2,5-dimethoxy-1,4-phenylene)bis(ethene-2,1-diyl)dibenzoic acid (H$_2$-PVDC) (86.0 mg, 0.20 mmol) in DMF (4 mL) was added to a solution of Yb(NO$_3$)$_3$.5H$_2$O (22.5 mg, 0.05 mmol) and 1M HNO$_{3(aq)}$ (10 ☒ L) in DMF (1 mL) to yield a neon green solution. The vial was capped and placed in an 105° C. isotemp oven for 36 hours to produce orange block-like crystals of the product. The crystals were collected, washed with DMF (4×5 mL) and air dried (48 mg, 51.9%).

EA Calcd. (%) for Yb$_2$(C$_{26}$H$_{20}$O$_6$)$_3$.(DMF)$_{12}$(H$_2$O)$_{10}$: C, 50.93; H, 6.15; N, 6.25. Found: C, 50.95; H, 5.40; N, 6.47. EA. Calcd. (%) for the chloroform exchange product, Yb$_2$(C$_{26}$H$_{20}$O$_6$)$_3$.(CHCl$_3$)$_{7.5}$(H$_2$O)$_{0.5}$(DMF)$_{0.5}$: C, 40.62; H, 2.82; N, 0.27. Found: C, 40.66; H, 2.75; N, 0.23. FT-IR (KBr 4000-700 cm$^{-1}$): 3433 (br), 2930 (w), 1655 (DMF C=O, m), 1602 (s), 1536 (m), 1418 (COO$^-$, vs), 1208 (s), 1180 (w), 1103 (w), 1041 (w), 960 (trans =C—H, w), 862 (w), 780 cm$^{-1}$ (m).

The molecular formulas for the as-synthesized and chloroform-exchanged materials were determined through analysis of the X-ray crystal data and elemental analysis data. While the absolute framework composition is unambiguous, it is more difficult to obtain accurate estimations of the quantity of guest molecules within the pores. This problem is exacerbated by the fact that these materials have very large cavities which easily lose guest molecules upon standing. Therefore, it is difficult to directly compare the number of estimated guest molecules determined form EA and TGA. These reported formulas are the best possible match to the EA data.

Reacting Yb(NO$_3$)$_3$.5H$_2$O with H$_2$-PVDC yielded yellow needles of Yb-PVDC-1, formulated as [Yb$_2$(C$_{26}$H$_{20}$O$_6$)$_3$(H$_2$O)$_2$].(DMF)$_6$(H$_2$O)$_{8.5}$. The materials maintain crystallinity in a variety of solvents, including chloroform and dimethylformamide, as confirmed by complete solvent exchange experiments and powder X-ray diffraction studies.

Single crystal X-ray diffraction analysis revealed that Yb-PVDC-1 crystallizes in the high symmetry Fddd space group and is composed of infinite Yb-carboxylate chains that run along the a crystallographic direction (FIG. 1a-c). The chains consist of alternating octa- and hexa-coordinated Yb$^{3+}$, bridged together in a di-monodentate fashion via the carboxylates of three different PVDC linkers (FIGS. 1a,b). Two water molecules are terminally coordinated to the octa-coordinate Yb$^{3+}$. These chains are connected along the via the phenylene vinylene portion of the ligand resulting in the formation of large rhombus-shaped channels measuring approximately 24×40 Å (FIG. 1c).

Reacting Yb(NO$_3$)$_3$.5H$_2$O with H$_2$-PVDC yielded yellow needles of Yb-PVDC-1, formulated as [Yb$_2$(C$_{26}$H$_{20}$O$_6$)$_3$(H$_2$O)$_2$].(DMF)$_6$(H$_2$O)$_{8.5}$. The materials maintain crystallinity in a variety of solvents, including chloroform and dimethylformamide, as confirmed by complete solvent exchange experiments and powder X-ray diffraction studies.

Single crystal X-ray diffraction analysis revealed that Yb-PVDC-1 crystallizes in the high symmetry Fddd space group and is composed of infinite Yb-carboxylate chains that run along the a crystallographic direction (FIG. 1a-c). The chains consist of alternating octa- and hexa-coordinated Yb$^{3+}$, bridged together in a di-monodentate fashion via the carboxylates of three different PVDC linkers (FIGS. 1a,b). Two water molecules are terminally coordinated to the octa-coordinate Yb$^{3+}$. These chains are connected along the [110] via the phenylene vinylene portion of the ligand resulting in the formation of large rhombus-shaped channels measuring approximately 24×40 Å (FIG. 1c).

The UV-Visible absorbance, emission, and excitation spectra were measured for Yb-PVDC-1 and compared to corresponding spectra for $H_2$-PVDC and an Yb-PVDC molecular complex (see supporting information) to determine how the MOF structure impacts the luminescence properties of the system. The absorbance spectrum of $H_2$-PVDC displays two bands with apparent maxima centered at 340 and 415 nm. Excitation through either of these bands produces a fluorescence band centered at 485 nm.

The excitation spectrum recorded upon this fluorescence band shows a profile similar to the absorbance spectrum. The Yb-PVDC molecular complex displays $Yb^{3+}$ emission in the NIR range, with a typical apparent maximum of the band at 980 nm. The excitation spectrum for the complex collected upon monitoring $Yb^{3+}$ emission (FIG. 1e) also contains two bands, centered at 340 and 415 nm, which adopt the same profile as the absorbance of $H_2$-PVDC, indicating that PVDC effectively sensitizes $Yb^{3+}$ via the antennae effect.

Luminescence analysis of crystalline Yb-PVDC-1 (chloroformexchanged material) displays $Yb^{3+}$ luminescence in the NIR (FIG. 1e). The MOF excitation spectrum is notably red-shifted, displaying bands with maxima at 370 and 470 nm (FIG. 1e). The apparent maximum of the excitation band shifts from 415 nm for the Yb-PVDC complex to 470 nm for Yb-PVDC-1, which is a significant change.

Although the Yb-PVDC complex experiments were performed in DMSO due to solubility constraints, this observed shift over 50 nm can not solely be attributed to solvatochromic effects. Rather, the inventors attribute a significant component of this shift to organizational constraints the MOF architecture imparts on the phenylene vinylene linkers. In Yb-PVDC-1, the ligands are arranged in parallel along [110], which may allow for weak interactions between neighboring ligands (FIG. 1d). These interactions are hypothesized to affect the electronic structure of the chromophore, resulting in a decrease of the excitation energy of the antennae.

To evaluate the extent to which ligand-ligand interactions impact the excitation and emission properties of Yb-PVDC systems, we prepared a second MOF, Yb-PVDC-2, formulated as $[Yb_2(C_{26}H_{20}O_6)_3] \cdot (DMF)_{12}(H_2O)_{10}$. Yb-PVDC-2 crystallizes in the orthorhombic Pnna space group and also exhibits infinite Yb-carboxylate SBUs. However, the connectivity within the SBU differs from that of Yb-PVDC-1. The SBU is composed of alternating octa- and hexa-coordinated $Yb^{3+}$. The $Yb^{3+}$ are bridged by two carboxylates in a dimondondentate fashion and by a third carboxylate that chelates the octa-coordinate $Yb^{3+}$ and coordinates in a monodentate fashion to the hexa-coordinate $Yb^{3+}$ (FIGS. 2a,b). These coordination modes result in a chain of cornersharing polyhedral $Yb^{3+}$. Each chain is linked to six other chains via the phenylene vinylene portion of the PVDC linkers (FIG. 2c). The linkers connecting the chains along the [001] stack in parallel, while those that connect the chains in the [011] form criss-crossing pairs with close π-π interactions (3-3.5 Å) between the central phenyl rings of the PVDC linkers (FIG. 2d). Because each infinite SBU is connected to six other SBUs, the resulting triangular channels are smaller than those observed for Yb-PVDC-1, measuring ~13-14 Å from corner to edge (FIG. 2c).

The close π-π interactions prompted an examination of the luminescent properties of Yb-PVDC-2 (chloroform-exchanged material) to determine whether these interactions impact the photophysical properties of this system. The excitation spectrum collected upon monitoring the emission intensity of $Yb^{3+}$ luminescence at 980 nm displayed band maxima at 370 and 500 nm (FIG. 2e). The emission spectra collected in the NIR range upon excitation at these wavelengths produce characteristic $Yb^{3+}$ emission. Interestingly, the lowest energy excitation band of Yb-PVDC-2 is red-shifted from 470 nm in Yb-PVDC-1 to 500 nm. The close π-π interactions between the PVDC linkers may decrease the π→π* transition, resulting in a lowered excitation energy.

In addition to lower energy excitation, the quantum yield of Yb-PVDC-2, 1.8%, is among the highest values reported for $Yb^{3+}$ complexes. In addition to the benefits of lower energy excitation, as discussed above, the high quantum yield of these MOFs will further improve detection sensitivity for bioanalytical bio-imaging applications.

To determine whether the MOF architecture provides efficient protection for the lanthanide cations from solvent quenching and to quantify the intramolecular energy transfer of the systems, quantum yield values were measured (see Table 1), using an integration sphere. The quantum yield of Yb-PVDC-2 is five times higher than Yb-PVDC-1 when excited through the lower energy band (490 nm), indicating the improved efficiency of the π→π* transition for intramolecular energy transfer. The quantum yield of Yb-PVDC-2 is among the highest values reported so far for ytterbium systems under solvent. These quantum yields are global: the excitation is performed through the sensitizer and the emission is observed through the $Yb^{3+}$ cations that have two different coordination environments and levels of protection in both MOFs. In Yb-PVDC-1, the octa-coordinate $Yb^{3+}$ are coordinated by two water molecules which quench ytterbium emission and lower the global quantum yield.

The inventors monitored ytterbium-centered luminescence lifetimes in order further to determine the effectiveness of the MOFs in protecting the lanthanide cations from nonradiative deactivation. Both MOFs displayed multiexponential decay patterns and were best fit with four components (Table 1), which are tentatively attributed to four different lanthanide environments: the hexa-coordinate and octa-coordinate $Yb^{3+}$ sites within the core of the MOF structures and those along the terminating edges of the crystals, where the lanthanide cations are more exposed to sources of non-radiative deactivation.

TABLE 1

ABSOLUTE EMISSION QUANTUM YIELDS $(\Phi)^a$ AND LUMINESCENT LIFETIMES $(\tau_x, \mu s)^b$ OF $Yb^{3+}$ CENTERED EMISSION AT 980 NM FOR THE MOFs[c]

|  | $\Phi_{Yb}{}^d$ | $\tau_1{}^d$ | $\tau_2$ | $\tau_3$ | $\tau_4$ |
|---|---|---|---|---|---|
| Yb-PVDC-1 | 3.3 (±0.5) × $10^{-3}$ | 29 (±2) | 10 (±1) | 1.5 (±0.5) | 0.34 (±0.06) |
| Yb-PVDC-2 | 1.8 (±0.2) × $10^{-2}$ | 22 (±4) | 5.6 (±1.5) | 1.7 (±0.3) | 0.61 (±0.17) |

$^a\lambda_{ex}$ = 490 nm.
$^b\lambda_{ex}$ = 354 nm.
[c]MOFs as crystalline solids under chloroform.
$^d$Error included in parentheses.

The long component values are up to two times longer than the longest lifetimes reported for $Yb^{3+}$ molecular species in solution (see Section II, below). These luminescence lifetimes demonstrate that MOFs can provide coordination environments with better protection from quenching than molecular complexes.

Thus, it is illustrated that a MOF-based approach to sensitize NIR-emitting lanthanides results in materials with enhanced luminescence properties. Specifically, we have shown that chromophoric antennae molecules and NIR-emitting lanthanides can be assembled into rigid MOF structures that effectively control the coordination environments around the lanthanide cations and the arrangement of chromophoric antennae. Using this strategy, it was possible to obtain a lower energy excitation wavelength by modifying the 3-D MOF structure to allow for close π-π interactions between the chromophores. The intrinsic structures of the MOFs provide protection of the lanthanide cations from solvent vibrations. Finally, MOFs constitute rigid and organized polymetallic systems with high densities of sensitizing groups and lanthanide cations per unit of volume for enhanced emission intensity.

The Yb-centered luminescence lifetimes for Yb-PVDC-1 and Yb-PVDC-2 have been measured discussed above. The MOFs display multi-exponential lifetimes, with the longest values ranging from 22 μs to 29 μs. These lifetimes are significantly longer than those reported for other $Yb^{3+}$ complexes in solution (see Tables 2-9). The long luminescence lifetimes will improve the sensitivity of time-resolved measurements due to increases in the length of time that the signal can be integrated over. In addition, the electronics and timing circuitry necessary to achieve time-resolved measurements can be simplified for emitters with longer lifetimes, thereby decreasing instrumentation costs.

C. Synthesis of (1) $Er_{0.32}Yb_{0.68}$-PVDC-1; (2) $Er_{0.58}Yb_{0.42}$-PVDC-1; (3) $Er_{0.70}Yb_{0.30}$-PVDC-1; and (4) $Er_{0.81}Yb_{0.19}$-PVDC-1

(i) Synthesis of (1) $Er_{0.32}Yb_{0.68}$-PVDC-1 (1)

In a glass vial (4 mL), a solution of 4,4'-(1E,1E)-2,2'-(2,5-dimethoxy-1,4-phenylene)bis(ethene-2,1-diyl)dibenzoic acid ($H_2$-PVDC)[1] (8.60 mg, 0.020 mmol) in DMF (0.4 mL) was added to a solution of $Yb(NO_3)_3 \cdot 5H_2O$ (1.02 mg, 0.0025 mmol) in DMF (0.050 mL), $Er(NO_3)_3 \cdot 5H_2O$ (0.55 mg, 0.00125 mmol) in DMF (0.025 mL), and 1M $HNO_{3(aq)}$ (10.0 μl) to produce a neon green solution. The vial was capped and placed in a 100° C. isotemp oven for 72 hours to produce yellow crystalline needles. The crystals were collected, washed with DMF (4×3 mL), and air dried (2.1 mg, 52.8%).

EA Calcd. (%) for $(Er_{0.32}Yb_{0.68})_2(C_{26}H_{20}O_6)_3(H_2O)_2 \cdot (DMF)_5(H_2O)_5$: C, 52.71; H, 5.18; N, 3.30. Found: C, 52.79; H, 4.33; N, 2.94. FT-IR (KBr 4000-700 $cm^{-1}$): 3381 (br), 2933 (w), 1659 (DMF C=O, m), 1600 (s), 1536 (s), 1413 ($COO^-$, vs), 1258 (w), 1209 (s), 1180 (m), 1105 (w), 1042 (s), 962 (m), 865 (w), 780 (trans C=C—H, s), 709 $cm^{-1}$(w).

(ii) Synthesis of (2) $Er_{0.58}Yb_{0.42}$-PVDC-1 (2)

In a glass vial (4 mL), a solution of 4,4'-(1E,1'E)-2,2'-(2,5-dimethoxy-1,4-phenylene)bis(ethene-2,1-diyl)dibenzoic acid ($H_2$-PVDC) (8.60 mg, 0.020 mmol) in DMF (0.4 mL) was added to a solution of $Yb(NO_3)_3 \cdot 5H_2O$ (1.02 mg, 0.0025 mmol) in DMF (0.050 mL), $Er(NO_3)_3 \cdot 5H_2O$ (1.66 mg, 0.00375 mmol) in DMF (0.075 mL), and 1M $HNO_{3(aq)}$ (10.0 μL) to produce a neon green solution. The vial was capped and placed in a 100° C. isotemp oven for 72 hours to produce yellow crystalline needles. The crystals were collected, washed with DMF (4×3 mL), and air dried (4.6 mg, 31.4%).

EA Calcd. (%) for $(Er_{0.58}Yb_{0.42})_2(C_{26}H_{20}O_6)_3(H_2O)_2 \cdot (DMF)_{8.5}(H_2O)_5$: C, 52.41; H, 5.67; N, 5.02. Found: C, 52.50; H, 4.87; N, 4.45. FT-IR (KBr 4000-700 $cm^{-1}$): 3433 (br), 2934 (w), 1658 (DMF C=O, m), 1602 (s), 1534 (s), 1418 ($COO^-$, vs), 1256 (w), 1210 (s), 1181 (w), 1106 (w), 1043 (s), 963 (m), 866 (w), 781 (trans C=C—H, s), 709 $cm^{-1}$(w).

(iii) Synthesis of $Er_{0.70}Yb_{0.30}$-PVDC-1 (3)

In a glass vial (4 mL), a solution of 4,4'-(1E,1'E)-2,2'-(2,5-dimethoxy-1,4-phenylene)bis(ethene-2,1-diyl)dibenzoic acid ($H_2$-PVDC) (8.60 mg, 0.020 mmol) in DMF (0.4 mL) was added to a solution of $Yb(NO_3)_3 \cdot 5H_2O$ (1.02 mg, 0.0025 mmol) in DMF (0.050 mL), $Er(NO_3)_3 \cdot 5H_2O$ (2.77 mg, 0.00625 mmol) in DMF (0.125 mL), and 1M $HNO_{3(aq)}$ (10.0 μL) to produce a neon green solution. The vial was capped and placed in a 100° C. isotemp oven for 72 hours to produce yellow crystalline needles. The crystals were collected, washed with DMF (4×3 mL), and air dried (2.3 mg, 9.9%)

EA Calcd. (%) for $(Er_{0.70}Yb_{0.30})_2(C_{26}H_{20}O_6)_3(H_2O)_2 \cdot (DMF)_{12}(H_2O)_7$: C, 51.43; H, 6.13; N, 6.31. Found: C, 51.42; H, 5.51; N, 6.65. FT-IR (KBr 4000-700 $cm^{-1}$): 3436 (br), 2935 (w), 1656 (DMF C=O, m), 1602 (s), 1542 (s), 1411 ($COO^-$, vs), 1259 (w), 1209 (s), 1180 (w), 1104 (w), 1043 (s), 947 (m), 865 (w), 780 (trans C=C—H, s), 709 $cm^{-1}$(w).

(iv) Synthesis of $Er_{0.81}Yb_{0.19}$-PVDC-1 (4)

In a glass vial (4 mL), a solution of 4,4'-(1E,1'E)-2,2'-(2,5-dimethoxy-1,4-phenylene)bis(ethene-2,1-diyl)dibenzoic acid ($H_2$-PVDC) (8.60 mg, 0.020 mmol) in DMF (0.4 mL) was added to a solution of $Yb(NO_3)_3 \cdot 5H_2O$ (0.56 mg, 0.00125 mmol) in DMF (0.025 mL), $Er(NO_3)_3 \cdot 5H_2O$ (2.77 mg, 0.00625 mmol) in DMF (0.125 mL), and 1M $HNO_{3(aq)}$ (10.0 μL) to produce a neon green solution. The vial was capped and placed in a 100° C. isotemp oven for 72 hours to produce yellow crystalline needles. The crystals were collected, washed with DMF (4×3 mL), and air dried (5.8 mg, 70.7%).

EA Calcd. (%) for $(Er_{0.81}Yb_{0.19})_2(C_{26}H_{20}O_6)_3(H_2O)_2 \cdot (DMF)_6(H_2O)_5$: C, 52.73; H, 5.35; N, 3.84. Found: C, 52.87; H, 4.73; N, 4.35. FT-IR (KBr 4000-700 $cm^{-1}$): 3399 (br), 2933 (w), 1656 (DMF C=O, m), 1602 (s), 1535 (s), 1416 ($COO^-$, vs), 1259 (w), 1209 (s), 1180 (w), 1106 (s), 1043 (s), 962 (m), 865 (w), 779 (trans C=C—H, s), 709 $cm^{-1}$(w).

Each framework is isomorphous with Yb-PVDC-1, as revealed by comparison of their respective powder X-ray diffraction patterns. The lanthanide composition in the products was determined by energy dispersive X-ray spectroscopy (EDS) and directly correlates to the amounts of each lanthanide salt used during synthesis (Table 1).

TABLE 1

Relative $Ln^{3+}$ content for the $Er_xYb_{1-x}$-PVDC-1 MOFs during synthesis ($\%_{Theo}$) and as determined by EDS in the final product ($\%_{Act}$)

| | PVDC | $Er(NO_3)_3$ | $Yb(NO_3)_3$ | $\%_{Theo}Er^{3+}$ | $\%_{Act}Er^{3+}$ |
|---|---|---|---|---|---|
| 1 | 0.02 | 0.00125 | 0.0025 | 33 | 32 (±2)[2] |
| 2 | 0.02 | 0.00375 | 0.0025 | 60 | 58 (±2) |
| 3 | 0.02 | 0.00625 | 0.0025 | 71 | 70 (±2) |
| 4 | 0.02 | 0.00625 | 0.00125 | 83 | 81 (±3) |

[a]Concentrations in mmol,
[b]errors in parentheses

The EDS measurements were performed on a minimum of four independently synthesized samples for each MOF and showed highly reproducible results for each lanthanide composition. These results indicate that any desired lanthanide composition can be produced in a predictable fashion, simply by controlling the stoichiometry of the reactants. The results also indicate that the MOF structure does not preferentially include either lanthanide cation; hence, any Er:Yb ratio can be targeted. This predictable aspect of the synthesis is highly advantageous for a barcoded material, and in this context it allows for the preparation of multiple barcodes simply by varying the ratios of two emitters.

Photoluminescence studies were performed on each sample to determine whether the different lanthanide compositions would result in materials having unique and discernible barcoded signals. MOFs 1-4 were suspended in chloroform and their excitation and emission spectra were measured. The MOFs display both erbium and ytterbium luminescence. The excitation spectrum of either the erbium or ytterbium emission band contains two bands with maxima at 370 and 470 nm, similar to Yb-PVDC1. Excitation through either of these bands simultaneously produces the characteristic $Yb^{3+}$ emission band centered at 980 nm and the $Er^{3+}$ band centered at 1530 nm in the NIR. As expected, increasing the amount of $Er^{3+}$ and decreasing the amount of $Yb^{3+}$ affected their respective emission intensities by the same token. This demonstrates that, by controlling lanthanide composition in keeping with the invention, one can effectively control the resulting luminescence intensities.

A plot of the ratio of the integrated intensities of the two different lanthanides with respect to their atomic ratio reveals a linear relationship. This trend is similar when either excitation band is used and is reproducible across multiple samples. For practical applications, this feature provides the option of using two excitation sources for verifying an encryption tag. Importantly, PXRD shows that these crystals maintain their crystallinity throughout the important requirement for applications.

Since the $Er^{3+}$ and $Yb^{3+}$ luminescence bands are in the NIR range, they can not be seen by the naked eye. Therefore, the signal can be monitored spectroscopically only, and the signal intensities artificially correlated with two different visible colors, for facile human observation. For example, purple could be used to represent the $Er^{3+}$ signal and green the $Yb^{3+}$ signal. Their relative intensities also could be reflected in a display. This would create four distinct barcodes correlating to each MOF.

The number and diversity (i.e., the combination) of barcodes can be increased, pursuant to the invention, by using more metal:metal ratios or by incorporating additional lanthanides into the material. To demonstrate this latter concept, $Er_{0.58}Nd_{xx}Yb_{0.42}$-PVDC-1 (5) was prepared and, as expected, it displayed a more complex barcode of NIR signals from its three component lanthanide cations.

For practical applications, barcoded (marked) articles of manufacture must be incorporated in ways that do not detrimentally affect their signal. As a preliminary test to evaluate the possibility of incorporating MOFs into actual materials, we coated 2 (Table 1) on a microscope slide with an adhesive, and then investigated its luminescence properties. Upon excitation at 490 nm the $Yb^{3+}/Er^{3+}$ barcode (mark) was easily detected in the NIR range.

Marking an article of manufacture with a MOF can be effected via various technologies, including but not limited to conventional printing, spin coating, safety threads and adhesion to an article of manufacture.

The MOF formulation selected is dependent on the marking technology used. Solid as well as and viscous liquid formulations, arc employed in a number of marking technologies, depending on the material being marked. The MOF is prepared, isolated in crystal form in the conventional manner, and then dried. Formulation of the MOF is achieved by dissolving the complex in a suitable organic or aqueous solution. Organic solvent in this case includes alcohol, amine, ether aromatic, alkane and alkene or a mixtures therein. Aqueous solution in this case denotes acidic to basic pH solutions prepared from known acids and bases. Solutions can then be concentrated to a viscous liquid or an emulsion prior to the application process of choice. Alternatively, formulation can achieved by combining the viscous liquid with a binder such as acrylic polyamide, polyurethane, polyester, polyethylene or an adhesive. The marking technology employed is discussed in detail below, which as mentioned employs a specifically tailored formulation.

Marking an article of manufacture with a MOF in a dried crystalline state can be accomplished by coating the MOF with an adhesive to secure the MOF to the article of manufacture. Alternatively, the dried crystalline MOF can be deposited in a clear tube or similar small clear container, and secured to the article of manufacture with an adhesive. Emulsions of the MOF are used to mark items such as safety threads, which is then incorporated into an identity card, bank note, check or currency. Furthermore, an organic viscous liquid form of the MOF is combined with a binder and used for spin coating a polymer film or fiber. The aqueous or organic viscous liquid form of the MOF is used in a conventional printing system, to mark an article of manufacture. Lastly, a viscous liquid form of the MOF is smeared with a tool or device on an article of manufacture and then coated with an adhesive.

TABLE 2

Polydentate triphenylene-functionalized complexes[1]

| Lanthanide | Ligand | solvent | t (µs) |
|---|---|---|---|
| Yb | terphenyl (1) | DMSO | 9.1 |
| Yb | triphenylene (2) | DMSO | 9.4 |

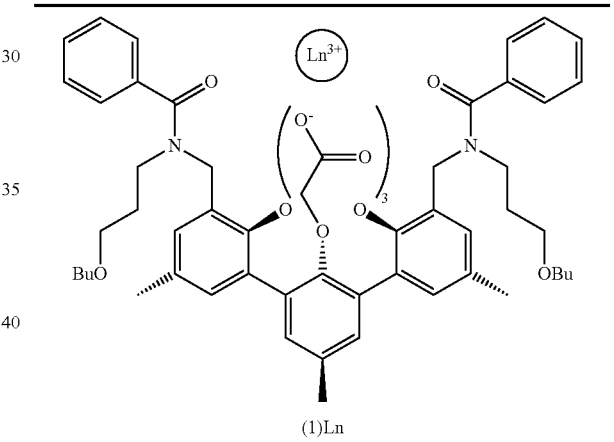

(1)Ln

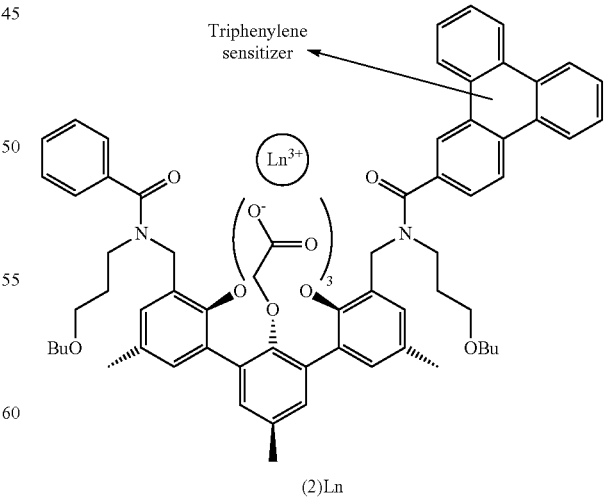

(2)Ln

Schematical representation of the terphenyl-based complex (1)Ln and its triphenylene-functionalized derivative (2)Ln TABLE 3
Pyrene sensitizers[2]
| | Ligand | solvent | t (μs) |
|---|---|---|---|
| Yb | [L1YbL2]- | water | 0.72 |
| Yb | YbL3 | water | 0.74 |
| Yb | YbL4 | water | 1.34 |
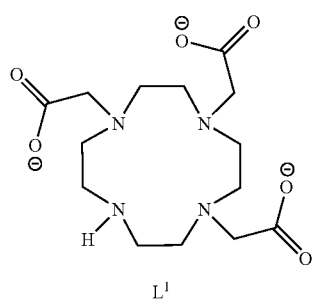 [SMILES: O=C([O-])CN1CCNCCN(CC(=O)[O-])CCN(CC(=O)[O-])CC1]
L[1]
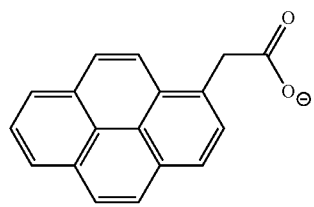
L[2]
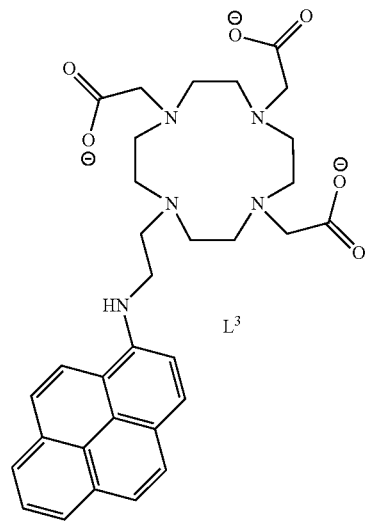 [SMILES: O=C([O-])CN1CCN(CCNc2ccc3ccc4cccc5ccc2c3c45)CCN(CC(=O)[O-])CCN(CC(=O)[O-])CC1]
L[3]
TABLE 3-continued
Pyrene sensitizers[2]
| Ligand | solvent | t (μs) |
|---|---|---|
L[4]
Structures of Ligands
TABLE 4
Dye sensitizers[3]
| | Ligand | solvent | t (μs) |
|---|---|---|---|
| Yb | H4(fluorescein) | Methanol | 9.8 |
| Yb | Br4(eosin) | Methanol | 11.6 |
| Yb | I4(erythrosin) | Methanol | 10.2 |
| Yb | Fluoreson | Methanol | 2.47 |

TABLE 4-continued
Dye sensitizers[3]
| Ligand | solvent | t (μs) |
|---|---|---|
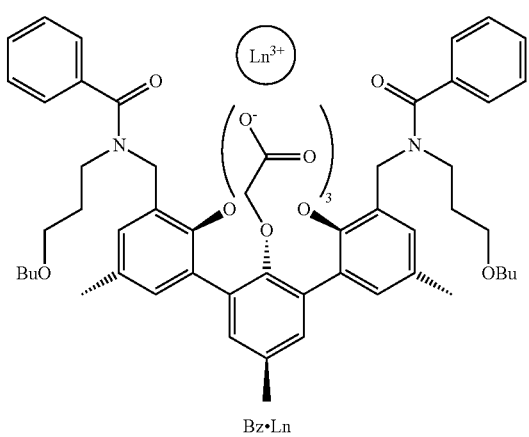
Fluorexon (Fx)
Terphenyl complexes functionalized with fluorescein, eosin, and erythrosin
TABLE 5
Poly(pyrazolyl)borate ligands[4]
| | Ligand | solvent | t (μs) |
|---|---|---|---|
| Yb | [Yb(L1)(NO3)2] | methanol | 1.58 |
| Yb | [Yb(L2)(NO3)] | methanol | 0.45, 1.36 |
| Yb | [Yb(L1)(dpm)2] | methanol | 2.94 |
| Yb | [Yb(L1)2][BPh4] | methanol | 2.01 |
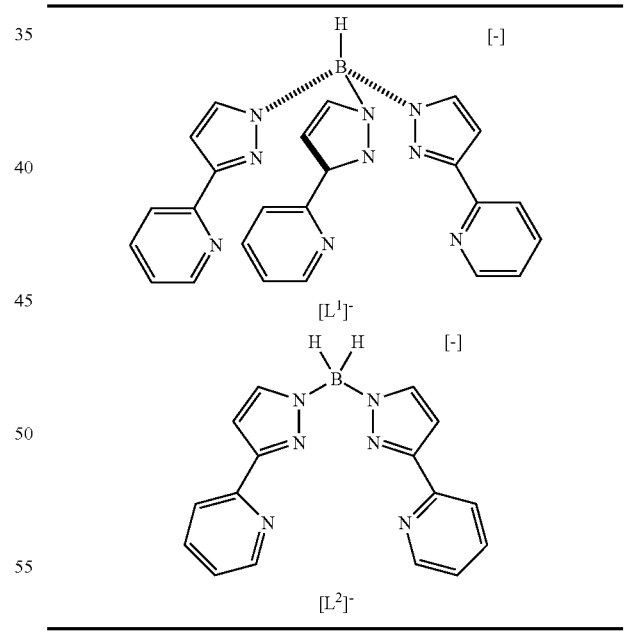
TABLE 6
Podates[5]
| | Ligand | solvent | t (μs) |
|---|---|---|---|
| Yb | [YbH2Tsox]$^{3-}$ | water | 2.21(1) |
| Yb | [YbH2TsoxMe]$^{3-}$ | water | 5.79(1) |

TABLE 6-continued

| | Podates[5] | | |
|---|---|---|---|
| | Ligand | solvent | t (µs) |
| Yb | [YbH2Tsox]$^{3-}$ & Triton X-100 | water | 2.82(1) |
| Yb | [YbH2TsoxMe]$^{3-}$ | water | 6.42(3) |

R = H,   Z = H    Tox
R = SO$_3^-$  Z = H    Tsox = (H$_4$L)$^{4-}$
         Z = Me   TsoxMe = (H$_4$L$^{Me}$)$^{4-}$

TABLE 7

| | Lehn cryptand[6] | | |
|---|---|---|---|
| | Lanthanide | solvent | t (µs) |
| Yb | Lehn Cryptand | water | 0.52 |

Synthesis of L$^1$ and its complexes

TABLE 8

| | Poly(pyrazolyl)borate and 1,3-diketonate ligands[7] | | |
|---|---|---|---|
| Lanthanide | Ligand | solvent | t-H (µs) |
| Yb | [M(L2)(dbm)2] | CH2Cl2 | 11.2 |
| Yb | [M(L2)(dbm)2] | CH3OH | 8.95, 1.27 |

TABLE 8-continued

Poly(pyrazolyl)borate and 1,3-diketonate ligands[7]

| Lanthanide | Ligand | solvent | t-H (µs) |
|---|---|---|---|

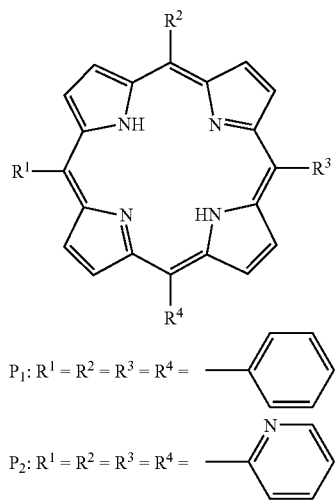

[L¹]⁻

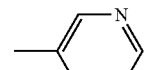

[L²]⁻

TABLE 9

Porphyrins[8]

| Lanthanide | Ligand | solvent | t-H (µs) |
|---|---|---|---|
| Yb | P1 | CH3OH | 4.8 |
| Yb | P2 | CH3OH | 7.8 |
| Yb | P3 | CH3OH | 8.2 |
| Yb | P4 | CH3OH | 12.1 |
| Yb | P5 | CH3OH | 1.7 |
| Yb | P6 | CH3OH | 1.1 |
| Yb | P7 | CH3OH | 0.9 |
| Yb | P8 | CH3OH | 0.9 |
| Yb | P9 | CH3OH | 1.1 |
| Yb | P10 | CH3OH | 2.1 |
| Yb | P11 | CH3OH | 2.3 |
| Yb | P12 | CH3OH | 5.6 |

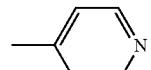

$P_1: R^1 = R^2 = R^3 = R^4 =$ 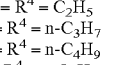

$P_2: R^1 = R^2 = R^3 = R^4 =$ 

TABLE 9-continued

Porphyrins[8]

| Lanthanide | Ligand | solvent | t-H (µs) |
|---|---|---|---|

$P_3: R^1 = R^2 = R^3 = R^4 =$ 

$P_4: R^1 = R^2 = R^3 = R^4 =$ 

$P_5: R^1 = R^2 = R^3 = R^4 = C_2H_5$
$P_6: R^1 = R^2 = R^3 = R^4 = n\text{-}C_3H_7$
$P_7: R^1 = R^2 = R^3 = R^4 = n\text{-}C_4H_9$
$P_8: R^1 = R^2 = R^3 = R^4 = n\text{-}C_9H_{19}$ $P_9: R^1 =$ , $R^2 = R^3 = R^4 = {}_H\text{-}C_9H_{19}$ $P_{10}: R^1 = R^3 =$ , $R^2 = R^4 = {}_H\text{-}C_9H_{19}$ $P_{11}: R^1 = R^2 =$ , $R^3 = R^4 = {}_H\text{-}C_9H_{19}$ $P_{12}: R^1 = R^2 = R^3 =$ , $R^4 = {}_H\text{-}C_9H_{19}$

What is claimed is:

1. A method for marking an object with a metal-organic complex, comprising:
   (a) providing a composition comprised of (A) a metal-organic framework comprised of complexes between two or more different lanthanides and an organic ligand, wherein said lanthanides are present in a predetermined ratio, wherein said ligand has multiple metal-binding sites and an electronic structure that accommodates a transfer of energy to said lanthanides, and wherein said complex, upon the transfer of energy to said lanthanides, emits electromagnetic radiation having emission maxima of at least 640 nm, and (B) at least one component selected from the group consisting of an adhesive and a binder, wherein said ligand is (4,4'-[(2,5-dimethoxy-1,4-phenylene)di-2,1-ethenediyl]bis-carboxylate); and then
   (b) applying said composition to said object.

2. A method according to claim 1, wherein said applying comprises loading a device with said composition and then using said device to mark said object with said composition.

3. A method of preparing a metal-organic complex, comprising:
   (a) providing an organic ligand that binds to a lanthanide, wherein said ligand has multiple metal-binding sites and an electronic structure that accommodates transfer of energy to said lanthanide;
   (b) reacting said ligand and two or more different lanthanides in a reaction mixture to form a metal-organic framework comprised of complexes between said two or more different lanthanides and said ligand, such that the distance between said ligand and said two or more different lanthanides in said complex is controlled; and wherein said complex, upon the transfer of energy to said lanthanides, emits electromagnetic radiation having emission maxima of at least 640 nm, wherein said ligand is (4,4'-[(2,5-dimethoxy-1,4-phenylene)di-2,1-ethenediyl]bis-carboxylate); and then (c) crystallizing said complex from said reaction mixture, forming crystals of said complex.

4. A method according to claim 3, further comprising isolating said crystals from said reaction mixture.

5. A composition comprising (A) a metal-organic framework comprised of complexes between two or more different lanthanides and an organic ligand, wherein said ligand has multiple metal-binding sites and an electronic structure that accommodates a transfer of energy to said lanthanides, and wherein said complex, upon the transfer of energy to said lanthanides, emits electromagnetic radiation having emission maxima of at least 640 nm, and (B) at least one component selected from the group consisting of an adhesive and a binder; wherein said ligand is (4,4'-[(2,5-dimethoxy-1,4-phenylene)di-2,1-ethenediyl]bis-carboxylate).

6. The composition according to claim 5, wherein said complex is of three or more different lanthanides and the organic ligand.

7. The composition according to claim 5, wherein said complex, upon transfer of energy to said lanthanides, emits electromagnetic radiation having emission maxima of at least 980 nm.

8. The composition according to claim 5, wherein said lanthanides are selected from the group consisting of erbium, ytterbium, and neodymium.

9. The composition according to claim 5, wherein said lanthanides are selected from the group consisting of samarium, holmium, thulium, praseodymium and dysprosium.

10. The composition according to claim 5, wherein said component is an adhesive.

11. The composition according to claim 5, wherein said component is a binder.

12. The composition according to claim 11, wherein the binder is selected from the group consisting of acrylic polyamide, polyurethane, polyester, and polyethylene.

13. A composition comprising (A) a complex of two or more different lanthanides and an organic ligand, wherein said ligand has multiple metal-binding sites and an electronic structure that accommodates a transfer of energy to said lanthanides, and wherein said complex, upon the transfer of energy to said lanthanides, emits electromagnetic radiation having emission maxima of at least 640 nm, and (B) at least one component selected from the group consisting of an adhesive and a binder, wherein said ligand is (4,4'-[(2,5-dimethoxy-1,4-phenylene)di-2,1-ethenediyl]bis-carboxylate).

14. The composition according to claim 13, wherein said composition has the formula $(Er_xYb_y)_2(4,4'-[(2,5-dimethoxy-1,4-phenylene)di-2,1-ethenediyl]bis-carboxylate)_3$, where:
x is a number between 0 and 1; and
y is a number having a value equal to (1−x).

15. The composition according to claim 14, wherein x is 0.81, 0.7, 0.58, or 0.32 and y is 0.19, 0.3, 0.42, or 0.68.

16. An object comprising an article of manufacture and, applied thereto, a composition according to claim 13.

17. The object according to claim 16, wherein said article of manufacture is a parcel, mechanical part, biological sample, electronic chip card, check card, credit card, identity card, bank note, certificate, or document.

18. The object according to claim 17, wherein said composition has the formula $(Er_xYb_y)_2(4,4'-[(2,5-dimethoxy-1,4-phenylene)di-2,1-ethenediyl]bis-carboxylate)_3$,
where:
x is a number between 0 and 1; and
y is a number having a value equal to (1−x).

19. The object according to claim 18, wherein x is 0.81, 0.7, 0.58, or 0.32 and y is 0.19, 0.3, 0.42, or 0.68.

* * * * *